US012605119B2

(12) United States Patent
Polak et al.

(10) Patent No.: US 12,605,119 B2
(45) Date of Patent: Apr. 21, 2026

(54) GENERATING A MOTION-CORRECTED MAGNETIC RESONANCE IMAGE DATASET

(71) Applicants: Siemens Healthcare GmbH, Erlangen (DE); The General Hospital Corporation, Boston, MA (US)

(72) Inventors: Daniel Polak, Erlangen (DE); Daniel Nicolas Splitthoff, Uttenreuth (DE); Stephen Farman Cauley, Winchester, MA (US)

(73) Assignees: Siemens Healthineers AG, Forchheim (DE); The General Hospital Corporation, Boston, MA (US)

( * ) Notice: Subject to any disclaimer, the term of this patent is extended or adjusted under 35 U.S.C. 154(b) by 352 days.

(21) Appl. No.: 18/521,089

(22) Filed: Nov. 28, 2023

(65) Prior Publication Data

US 2024/0206819 A1 Jun. 27, 2024

(30) Foreign Application Priority Data

Dec. 27, 2022 (EP) .................................... 22216716

(51) Int. Cl.
　G06K 9/00 (2022.01)
　A61B 5/00 (2006.01)
(Continued)

(52) U.S. Cl.
　CPC .............. A61B 5/7207 (2013.01); G06T 7/20 (2013.01); G06T 7/30 (2017.01); G06T 11/005 (2013.01); *G06T 2207/30241* (2013.01)

(58) Field of Classification Search
　CPC . G06T 7/20; G06T 11/005; G06T 7/30; G06T 2207/30241; G01R 33/5676;
(Continued)

(56) References Cited

U.S. PATENT DOCUMENTS

| | | | | |
|---|---|---|---|---|
| 8,155,389 B2 * | 4/2012 | Parker | ...................... | G06T 5/50 |
| | | | | 382/128 |
| 2021/0373105 A1 | 12/2021 | Polak et al. | | |
| 2022/0065971 A1 | 3/2022 | Polak | | |

OTHER PUBLICATIONS

Polak, D., Splitthoff, D. N., Clifford, B., Lo, W. C., Huang, S. Y., Conklin, J., . . . & Cauley, S. (2021). Scout Accelerated Motion Estimation and Reduction (SAMER). Magnetic resonance in medicine, 87(1), 163. (Year: 2021).*

(Continued)

*Primary Examiner* — Gregory A Morse
*Assistant Examiner* — Kevin M Coomber
(74) *Attorney, Agent, or Firm* — Lempia Summerfield Katz LLC

(57) ABSTRACT

A method for generating a motion-corrected MR image dataset of a subject includes: acquiring k-space data of an MR image of a subject in an imaging sequence; acquiring at least two low-resolution scout images of the subject interleaved with the k-space data of the imaging sequence; comparing the scout images with one another in order to detect and/or to estimate subject motion between the scout images; and reconstructing a motion-corrected MR image dataset from the k-space data acquired in the imaging sequence. The reconstruction process includes: estimating the motion trajectory of the subject by comparing the k-space data with at least one of the low-resolution scout images; and estimating the motion-corrected image dataset using the estimated motion trajectory, wherein the estimations involve minimizing the data consistency error between the acquired k-space data and a forward model described by an encoding operator.

13 Claims, 6 Drawing Sheets

(51) Int. Cl.
    *G06T 7/20*          (2017.01)
    *G06T 7/30*          (2017.01)
    *G06T 11/00*        (2006.01)

(58) Field of Classification Search
    CPC . G01R 33/5611; G01R 33/4818; A61B 5/055;
                             A61B 5/7207
    See application file for complete search history.

(56) References Cited

OTHER PUBLICATIONS

Lin, W., Nielsen, T., Qin, Q., Mostofsky, S. H., Wei, J., Huang, F., & Duensing, G. R. (2014). Real-time motion correction in two-dimensional multislice imaging with through-plane navigator. Magnetic resonance in medicine, 71(6), 1995-2005. (Year: 2014).*

Cordero-Grande L., et al., "Motion-corrected MRI with DISOR-DER: Distributed and incoherent sample orders for reconstruction deblurring using encoding redundancy", Magn Reson Med. 2020; 84, pp. 713-726.

Cordero-Grande L., et al. "Sensitivity Encoding for Aligned Multishot Magnetic Resonance Reconstruction" IEEE Transactions on Computational Imaging, vol. 2, No. 3, Sep. 2016, pp. 266-280.

Cordero-Grande L., et al., "Three-dimensional motion corrected sensitivity encoding reconstruction for multi-shot multi-slice MRI: application to neonatal brain imaging. Magnetic Resonance in Medicine", 2018, 79. Jg., Nr. 3, pp. 1365-1376.

Hamilton, et al.: "Recent Advances in Parallel Imaging for MRI", Prog. Nucl. Magn. Reson. Spectrosc; 101, pp. 71-95 (2017).

Haskell, et al. "Targeted Motion Estimation and Reduction (TAMER): Data Consistency Based Motion Mitigation for MRI using a Reduced Model Joint Optimization" IEEE, vol. 37, Nr. 5, pp. 1253-1265, 2018.

Lin, et al., "Real-time motion correction in two-dimensional multislice imaging with through-plane navigator"; Magnetic resonance in medicine; vol. 71; No. 6; pp. 1995-2005; 2013.

Polak, Daniel, et al. "Scout accelerated motion estimation and reduction (SAMER)." Magnetic resonance in medicine 87.1 (2022): pp. 1-27.

Uecker, et al.: "ESPIRIT—An Eigenvalue Approach to Autocalibrating Parallel MRI: Where Sense Meets GRAPPA"; in Magnetic Resonance in Medicine; vol. 71; pp. 990-1001; 2014.

Pruessmann, et al., "SENSE: Sensitivity Encoding for Fast MRI", Magnetic Resonance in Medicine 42, pp. 952-962 (1999).

* cited by examiner $$[\hat{\chi}] = \text{argmin}_{\chi} \left\| E_{\hat{\theta}}\chi - s \right\|_2^2$$

$$[\hat{\theta}] = \text{argmin}_{\theta} \left\| E_{\theta}\hat{\chi} - s \right\|_2^2$$

22b  22a    25b  25a $$[\hat{\theta}_i] = \text{argmin}_{\theta i} \left\| E_{\theta i}\hat{\chi} - s_i \right\|_2^2 \quad \longleftarrow \quad 54$$

$$[\hat{\chi}] = \text{argmin}_{\chi} \left\| E_{\hat{\theta}}\chi - s \right\|_2^2 \quad \longleftarrow \quad 56$$

GENERATING A MOTION-CORRECTED MAGNETIC RESONANCE IMAGE DATASET

The present patent document claims the benefit of European Patent Application No. 22216716.5, filed Dec. 27, 2022, which is hereby incorporated by reference in its entirety.

TECHNICAL FIELD

The disclosure relates to a method for generating a motion-corrected magnetic resonance image, to a magnetic resonance imaging apparatus, and to a computer program and digital storage medium.

BACKGROUND

Patient motion may degrade the diagnostic quality of magnetic resonance (MR) exams. Fast imaging protocols may reduce the impact of motion. For example, parallel imaging techniques, (as summarized in J. Hamilton et al., "*Recent Advances in Parallel Imaging for MRI*," Prog. Nucl. Magn. Reson. Spectrosc., vol. 101, pp. 71-95, 2017), exploit the properties of modern multi-channel coil arrays to separate aliased pixels in the image domain or to estimate missing k-space data, using knowledge of nearby acquired k-space points, in order to allow scan time reduction by sampling a smaller number of phase encoding lines in k-space.

Some magnetic resonance imaging (MRI) motion correction techniques involve measuring the motion by tracking devices or navigator acquisitions.

By contrast, retrospective methods correct for motion artefacts after the data acquisition without disruptions to the sequence timing or inclusion of additional hardware. By including motion operations into the MR forward model, these techniques account for the patient's motion in the final image reconstruction and therefore reduce motion artefacts through improved model agreement. Data-driven retrospective correction techniques allow for the motion data to be derived from the acquired k-space data itself. In the case of parallel imaging, this is facilitated because the complex sensitivity profiles of multi-channel coil arrays inherently encode the patient position into the acquired k-space data. For multi-shot acquisitions, the goal in retrospective motion correction techniques is to extract the per shot motion parameters and the motion-free image simultaneously. This may be accomplished by either minimizing an image quality metric, such as image entropy, or by minimizing the data consistency error of a parallel "imaging+motion" forward model, (as described in L. Cordero-Grande et al., "*Three-dimensional motion corrected sensitivity encoding reconstruction for multi-shot multi-slice MRI: Application to neonatal brain imaging*," Magn. Reson. Med., vol. 79, no. 3, pp. 1365-1376, 2018; J. Cordero-Grandel et al., "*Sensitivity Encoding for Aligned Multishot Magnetic Resonance Reconstruction*," IEEE Trans. Comput. Imaging, vol. 2, no. 3, pp. 266-280, 2016; and M. W. Haskell et al., "*TArgeted Motion Estimation and Reduction (TAMER): Data consistency based motion mitigation for mri using a reduced model joint optimization*," IEEE Trans. Med. Imaging, vol. 37, no. 5, pp. 1253-1265, 2018). For the latter, the motion and image vector are jointly estimated via an inversion of the non-linear forward model. This corresponds to a large-scale non-linear optimization problem that may be computationally very expensive. Previously proposed methods alternate between optimizing just the image or the motion parameters while assuming the other to be fixed (see L. Cordero-Grande in Magn. Reson. Med.), instead of updating all optimization variables at once. Nevertheless, repeated updates of the imaging voxels lead to excessive computation that prohibits its use in clinical settings. When the "imaging+motion" model and the underlying imaging protocol also includes parallel imaging techniques which make use of the complex sensitivity profiles of multi-channel coil arrays, such as SENSE (SENSitivity Encoding) or ASSET (Array coil Spatial Sensitivity Encoding), it is referred to as "SENSE+motion" model.

In D. Polak et al., "Scout accelerated motion estimation and reduction (SAMER)," Magn. Reson. Med., vol. 87, pp. 163-178, 2022, a technique is described that utilizes a single rapid scout scan to drastically reduce the computation cost of motion estimation.

The scout image contains center of k-space information that is compared against the k-space data of the actual MR acquisition for each shot to derive the subject's motion. This corresponds to registration of the k-space data with the scout image in k-space. This strategy is used to completely avoid the alternating optimization of subject motion and image volume, which is otherwise required in retrospective motion correction techniques. In the SAMER-technique, the motion trajectory of the subject is first estimated, and the motion trajectory is then used in a motion-aware parallel image reconstruction, e.g., using a "SENSE+motion" model, to yield the motion-mitigated image. This reduces the computational costs by several orders of magnitude when compared to established alternating optimization method.

However, despite the computational benefits of the SAMER-technique, large patient motion may still be challenging, since the minimization problem is non-convex, i.e., the algorithm may converge towards a local minimum, rather than the global minimum, if the patient motion exceeds a certain magnitude. Thus, there is a demand for techniques which improve the robustness and speed of retrospective motion correction methods such as SAMER.

SUMMARY AND DESCRIPTION

It is thus an object of the disclosure to provide a method for generating a motion-corrected magnetic resonance (MR) image dataset of the subject, which uses a retrospective motion correction technique, and which allows a robust image reconstruction. It is a further object of the disclosure to provide a method for generating an MR image dataset of the subject which allows for rapid motion identification and estimation. "Retrospective" motion correction means that the method does not require tracking devices or disruptions in the imaging sequence, as would be posed by navigators.

These objects are met or exceeded by the method, the MRI apparatus, and the computer program disclosed herein. The scope of the present disclosure is defined solely by the appended claims and is not affected to any degree by the statements within this summary. The present embodiments may obviate one or more of the drawbacks or limitations in the related art.

A method for generating a motion-corrected MR image dataset of a subject is disclosed. The method includes: acquiring k-space data of an MR image of a subject in an imaging sequence; wherein at least two low-resolution scout images of the subject are acquired interleaved with the k-space data of the imaging sequence; comparing the scout images with one another in order to detect and/or to estimate subject motion between the scout images; and reconstructing a motion-corrected MR image dataset from the k-space data acquired in the imaging sequence by minimizing the data consistency error between the acquired k-space data and a forward model described by an encoding operator, wherein the encoding operator includes the motion trajectory of the subject during the imaging sequence, Fourier encoding, and optionally a phase operator, subsampling, and/or coil sensitivities of a multi-channel coil array. The minimization is executed by, in a first act, estimating the motion trajectory of the subject by comparing at least part of the k-space data with at least one of the low-resolution scout images, taking into account the detected or estimated subject motion between the scout images, and in a second act, estimating the motion-corrected image dataset using the motion trajectory estimated in the first act, wherein both acts include a minimization of the data consistency error between at least part of the acquired k-space data and the forward model.

The disclosure thus proposes to acquire multiple scout scans/images throughout the imaging scan by interleaving scouts with the standard MR image data acquisition. Thereby, the stability of retrospective motion-correction by the SAMER method is improved. While these additional scout scans increase the total scan time, they provide useful information which may be used to improve the stability and robustness of data-driven retrospective motion correction. In particular, the data from the scout scans may be used to improve the robustness of retrospective navigator-free motion estimation. Such retrospective motion-correction techniques, including SAMER, rely on a non-convex optimization that for large subject motion may be prone to local minima. To improve the convergence stability, it is desirable to "jump-start" the motion search using estimates of the patient's position during the imaging sequence. Such estimates may be obtained from the scout images acquired in intervals during the imaging sequence. For example, the initial scout image may be registered to the subsequent scout images, and the estimation of the motion trajectory may be jump-started from these motion estimates. Thereby, the convergence of the first act of the reconstruction method, i.e., the estimation of the motion trajectory of the subject, will converge faster and will be more robust.

The insertion of additional scout scans into the imaging sequence does not change the sequence timing within each echo train or each TR. Moreover, as opposed to volume navigators (vnav) this strategy does not affect image quality or contrast of the imaging scan. The scout images may be acquired with the same imaging sequence and the same contrast as the MR image acquired with the imaging sequence.

The method may be executed on any medical or other MRI apparatus. The subject may be a human or animal or a part thereof, in particular a patient to be examined or a part thereof.

The imaging sequence used to acquire the motion-corrected MR image may use any MR imaging protocol, for example, a two-dimensional (2D) or three-dimensional (3D) imaging protocol. In a 2D-imaging protocol, a slice of the subject is selected during radiofrequency (RF) excitation using a slice-select gradient. The k-space plane may be sampled by using a phase encoding gradient along one spatial dimension and a frequency encoding gradient along another spatial dimension. In a 3D-imaging protocol, a thick slab of tissue is excited together. In such 3D-imaging, spatial encoding may be performed using phase-encoding gradients along two spatial dimensions, also referred to as "phase-encode plane," and frequency encoding along the third spatial dimension, referred to as the readout direction. Accordingly, with each MR echo, a k-space line oriented along the readout direction is sampled. By modifying the phase-encoding gradient before each readout, it is possible to design different sampling orders, i.e., the order in which the k-space lines are acquired in the phase-encode plane. It has been found that the robustness and speed of retrospective motion estimation may be further improved by using optimized reordering schemes for rectilinear three-dimensional (3D) multi-shot acquisitions. "Reordering scheme," "reordering," or "sampling order" may refer to the order in which k-space lines are acquired, in particular the order in which the phase-encode plane is sampled, such as linear or radial. For example, L. Cordero-Grande et al., "*Motion-corrected MRI with DISORDER: Distributed and incoherent sample orders for reconstruction deblurring using encoding redundancy*," Magn. Reson. Med., vol. 84, pp. 713-726, 2020, propose a jittered checkerboard reordering scheme for 3D acquisitions (referred to herein as "checkered"). By uniformly distributing the samples of each shot across k-space, this reordering was shown to have computational advantages, including improved convergence stability and speed.

In the imaging sequence, several k-space lines may be acquired in each of a plurality of echo trains. An "echo train," also referred to as "shot," includes a plurality of MR echoes, e.g., spin echoes and/or gradient echoes. During each echo, a k-space line is acquired and there may be 8 to 512 echoes or 128 to 256 echoes in one echo train. An echo train may be acquired after a single preparation pulse, such as an inversion pulse. In most sequences, an echo train includes a preparation pulse, and then all echoes have their own excitation/refocusing pulses, except in echo-planar imaging. Thus, an echo train may refer to a series of gradient echoes or spin echoes, each echo corresponding to one line in k-space, which may be acquired after a single preparation pulse (as e.g., in MPRAGE) or without such preparation pulse (as in steady state sequences), but still in one sequence within an MR imaging protocol.

The imaging sequence may be a turbo-spin-echo sequence or a gradient-echo sequence. The imaging sequence may be a non-steady-state sequence, i.e., a sequence in which the signal intensity or contrast varies over the echo train, in particular due to T1 and/or T2 relaxation, e.g., MPRAGE. An echo train may include one or several sub echo trains, wherein a separate image may be acquired in each sub echo train. For example, in MP2RAGE, each echo train includes two sub echo trains, so that the data for two images with different contrast are acquired, one in each sub echo train. Alternatively, the disclosure may be used on steady state sequences, such as gradient recalled echo (GRE).

The imaging sequence may use a multi-shot method in which a fraction of k-space is sampled in one shot. The imaging protocol may include between 5 and 300 shots, depending on whether it is 2D or 3D. Examples for such imaging protocols are fast spin-echo sequences, also termed SPACE ("sampling perfection with application of optimized contrast using flip angle evolution") or MPRAGE ("magnetization prepared rapid gradient echo"), which uses an inversion preparation followed by gradient echoes. 2D imaging protocol such as 2D Turbo Spin-Echo may also be used.

The motion-corrected MR image may be an image useful for diagnosis. It may have a spatial resolution that is 4 to 32 times or 8 to 16 times, (by voxel volume) higher than that of the low-resolution scout image. The voxel size may be $0.5 \times 0.5$ mm$^2$ to $3 \times 3$ mm$^2$ or $1 \times 1$ to $2 \times 2$ mm$^2$ in the phase encode plane.

The low-resolution scout images may be acquired using the same imaging protocol as the k-space data of the diagnostic MR image. The contrast of the scout images may be the same as that of the diagnostic MR image because contrast matching is important for motion estimation. In certain embodiments, one low-resolution scout image may be acquired in one shot. The term "interleaved" means that at least one low-resolution scout image is acquired in between the k-space data of the imaging sequence, wherein another scout image may be acquired at the beginning, (i.e., before), or at the end, (e.g., directly after the k-space data of the imaging sequence). In other words, at least two scout images, (e.g., 2 to 10 or 3 to 5 scout images), are acquired throughout the imaging sequence. These additional scout scans are interleaved with the imaging sequence. For example, in MPRAGE, scout scans may be acquired every third to eighth, (e.g., every fourth, fifth, or sixth), repetition time (TR) and/or every third to eighth, (e.g., every fourth, fifth, or sixth) shot. By contrast, in the standard SAMER sequences, only a single scout scan is acquired either before or after the imaging sequence. In the present disclosure, at least one scout scan may be incorporated into the imaging sequence, in addition to a scout scan before and/or after. Multiple scout scans may be incorporated into the imaging sequence. Alternatively, there may be only two scout scans, one before and one after the imaging sequence.

The low-resolution scout images may have a spatial resolution of $2 \times 2$ mm$^2$ to $8 \times 8$ mm$^2$, $3 \times 3$ to $5 \times 5$ mm$^2$, or $4 \times 4$ mm$^2$ in the phase-encode plane. The scout images may be 2D or 3D images. The scout image may be acquired with the same imaging protocol or with a different imaging protocol than the MR image data to be used for the motion-corrected image, for example, a turbo spine-echo (e.g., MPRAGE) or gradient-echo (e.g., FLAIR) sequence, such as with a high parallel imaging acceleration of e.g., R=4-12. The scout image(s) may not be acquired in the same echo trains as the MR image data for the motion-corrected image.

The scout images are compared with one another in order to detect and/or to estimate subject motion between the scout images. The phrase "detect subject motion" may mean to infer whether patient motion has occurred at all between the scout images or not. This may be achieved by comparing either the k-space data or the image data of the individual scout scans that were acquired at different time points throughout the imaging sequence. Patient motion will reduce the data similarity, and one may predict the occurrence and possibility the severity of motion by using a pre-defined metric, e.g., the L1-norm, L2-norm, or using an artificial intelligence algorithm, e.g., based on machine learning, such as a neural network. The phrase "estimate subject motion" may mean that the magnitude and possible direction of the motion is estimated, for example, by performing a registration between the scout images. This may involve a registration of the second and any further scout images with the first scout image, in order to infer motion parameters between them, e.g., a set of 6 rigid-body motion parameters (3 translational parameters and 3 rotational motion parameters in 3D). Alternatively, non-rigid motion estimation is also possible from these scout images by performing a non-rigid registration. Thus, a rough motion trajectory may be inferred already from the scout images.

Further, the scout images may be used in retrospective motion correction of the acquired image data using a modified version of the SAMER method disclosed by D. Polak et al. in Magn. Reson. Med., vol. 87, pp. 163-178, 2022. That is, at least one of the scout images is used as the image estimate $\tilde{x}$ in the first act of the optimization. In this act, a set of motion parameters $\hat{\theta}_i$ may be estimated for a number of time points i, wherein each time point may correspond to one shot. This estimation may be done using the "SENSE+ motion" model on one of the scout images $\tilde{x}$ and comparing with the k-space data $s_i$ acquired around the time point i, for example in shot number i. The motion estimation also takes into account the estimated or detected subject motion between the scout images, in particular in order to "jump start" the motion search using estimates of the patient's position at the time points at which the scout images are acquired. Thereby, for example six rigid-body motion parameters $\hat{\theta}_i$ may be estimated for each time point i, wherein each time point may for example correspond to one echo train of the imaging sequence. In a second act of the image reconstruction, the motion parameters $\hat{\theta}_i$ are used to estimate the actual motion-corrected image from the acquired MR image data s, again using a "SENSE+motion" model.

According to an embodiment, the act of estimating subject motion between the scout images includes registering the scout images with one another to calculate subject motion between the scout images, e.g. in the form of (rigid-body) motion parameters. This may be done in image space. The motion trajectory of the subject may be estimated by comparing the part of the k-space data acquired close before and/or after each scout image with that scout image in order to estimate the motion trajectory of the subject during the acquisition of that part of the k-space data. This motion trajectory is then corrected with the subject motion (e.g., motion parameters) between the scout images, in order to yield the motion trajectory to be used in the second act of the image reconstruction.

This embodiment is advantageous, because, especially in case of relatively large movements, the first act of the retrospective motion correction may not converge to the true motion parameters, i.e., there is a chance that the gradient descent method will converge towards a local minimum. If, however, each part of the acquired k-space data is only compared to a scout image which was acquired close in time, the chances are better that the subject motion between the respective scout image and that part of the k-space data is still sufficiently small. Thus, in this embodiment, the different scout images are used as image estimates when comparing with the k-space data acquired close before and/or closely after that scout image. The thus obtained motion trajectory has then to be corrected with the subject motion between the scout images as so far only relative position changes with respect to the closest scout image that has been estimated. This subject motion may be obtained by registering the scout images with one another. Thereby, a more robust motion estimation and correction is possible.

According to another embodiment, the act of estimating subject motion between the scout images includes registering the second scout image and optionally each further scout image with the first scout image to estimate motion parameters between the scout images. The motion trajectory of the subject is estimated by comparing the acquired k-space data with the first scout image. The minimization uses the motion parameters estimated from the registration as a starting estimate for the motion trajectory for the part of the k-space data acquired close before and/or after the second and optionally each further scout image.

This embodiment is similar to the previous embodiment, but herein the image used as the image estimate $\tilde{x}$ in the first act of the optimization is the first scout image. Please note that "first" does not necessarily indicate that the scout image is the first scout image to be acquired. The scout image may be the first one acquired, but it may also be any of the other scout images. However, the other scout images are registered with respect to the first scout image, which is used as initial image estimate in the first act of the SAMER motion correction. However, when the different parts of the k-space data, which were acquired at different time points close to the second and optionally each further scout image, are compared with the k-space data from the first scout image, the motion parameters estimated from the registration are used as a starting point or first estimate, i.e., to "jump-start" the search for the correct motion trajectory of the subject. Jump-starting the motion search from these subject motion estimates may improve the convergence of the minimization problem and thus increase the robustness and speed of the act of reconstructing a motion-corrected MR image dataset, in particular of the first act.

According to an embodiment, the forward model is phase-aware and thus includes the effects of changes in the B0 field caused by subject motion during the imaging sequence.

This phase-aware forward model, which is used at least in the second act of the image reconstruction, may also make use of the scout scans in several ways. For example, based on the scout images, one may derive a model or phase operator that predicts the phase variations as a function of detected motion parameters, e.g., as a function of the motion trajectory. This phase operator may then be used in the image reconstruction, in particular in the second act (d2) of estimating a motion-corrected image dataset.

According to an embodiment, one or optionally several map(s) of phase differences are calculated between the first scout image and the second and optionally further scout image(s), and the map(s) of phase differences are used in the phase-aware estimation of the motion-corrected image dataset (x).

This may be done either by using the maps of phase differences directly in the estimation acts (d1) and/or (d2), in particular by using the closest matching maps of phase differences. In particular, the scout images allow estimation of phase maps corresponding to specific points in time. Interpolation along the time domain may also be performed to estimate phase maps for intermediate time points. Alternatively, the maps of phase differences may be used to calculate a model which predicts maps of phase differences as a function of motion parameters. This model may then be used in the act of estimating a motion-corrected image dataset.

In this embodiment, the scout data may also facilitate phase estimation and thus reduce artifacts that arise from B0 field inhomogeneity. In particular, in MR imaging of the head, with its air-filled cavities, the B0 field is inhomogeneous because of abrupt susceptibility changes between air and tissue. The B0 field is highly dependent on the position and orientation w.r.t to the main scanner magnetic field, so that the B0 field changes as a result of patient motion, in particular as a function of head position in head imaging.

In phase-sensitive sequences such as gradient echo sequences, in particular with a TE>15 ms, phase errors may lead to image distortions in the final image. Neglecting this effect during the final image reconstruction may lead to undesirable ghosting artifacts, because the reconstruction model does not accurately describe the acquired k-space data. It is difficult to estimate the motion-corrected image data set, e.g., in the second act of the SAMER minimization problem, by using a phase-aware forward model, because this minimization problem is highly ill-posed and computationally costly.

Here, the additional scout images may improve convergence, robustness, and speed of the estimation by providing additional k-space data across multiple time points and/or motion states. The additional k-space data may be used during phase estimation that may assume a low rank constraint over time (small changes over time). In addition, the scout data may be used to infer B0 phase changes directly through a comparison in image space.

The scout images may be first registered with one another before extracting the phase differences between them. This may be done by calculating a map of phase differences between the first scout image and the second scout image, as well as the further scout image(s) (if any). Thereby, the scout data may be used to infer the B0 phase changes directly through a comparison in image space.

This map(s) of phase differences may be used in the second act of estimating the motion-corrected image dataset, which uses both the motion trajectory estimated in the first act, and the map of phase differences between the respective scout images and includes a minimization of the data-consistency error between at least part of the acquired k-space data and a phase-aware forward model. In other words, background phase variations may be estimated from the at least two scout images acquired interleaved with the k-space data of the imaging sequence.

The optimization is thus carried out in 3 acts. In the first act, the motion trajectory of the subject is estimated as described herein. In the second act, the background phase variations are estimated. In the final act (now the third act), the motion-corrected image dataset is reconstructed using the motion trajectory and the phase estimation. In the final act, the motion-mitigated image is obtained from solving a motion-aware and phase-aware "SENSE+motion" forward model, also referred to as parallel imaging model, that accounts for potential B0 changes across the motion states.

According to an embodiment, the time interval between the acquisition of the scout images during the imaging sequence may be dynamically adapted depending on whether subject motion is detected.

As described above, the scout images may be used to infer the occurrence of subject motion, e.g., by comparing the k-space data or the image data of the scout scans acquired during the imaging sequence with one another, or alternatively by comparing the acquired k-space data with the last acquired scout scan, wherein the comparison takes place already during the imaging sequence. If this comparison identifies subject/patient motion, the MRI scanner may automatically initiate countermeasures, such as repeating the acquisition of part of the k-space data, informing the technician that the patient has moved, or retrospective or prospective motion correction methods. One may use a predefined metric, such as the L1-norm, in order to define a threshold above which patient motion is considered so severe that such countermeasures are taken.

According to an embodiment, the first act of the minimization is carried out during the image acquisition, and the time interval to the acquisition of the next scout image is adapted, depending on whether the estimated motion trajectory indicates strong or weak subject motion.

Thus, the time interval between successive scout scans may be adapted dynamically during the scan, i.e., during the acquisition of the MR image using the imaging sequence, to accommodate for the patient's individual motion behavior, in particular depending on whether the patient is still or motion-prone. This may be done by carrying out the first act of the image reconstruction already during the scan, wherein the k-space data which has just been acquired is compared with the k-space data of the last acquired scout image, in particular using a "SENSE+motion" model to estimate the motion trajectory. If this comparison gives the result that there has been no motion in the meantime, or the motion is below a pre-defined threshold, the imaging sequence may be continued without the acquisition of another scout image. If, however, the comparison of the k-space data with the last scout image shows a considerable magnitude of the motion trajectory, the acquisition of the next scout image may be triggered. Thereby, the time interval between the acquisitions of the scout images is adapted depending on whether the estimated motion trajectory indicates strong or weak subject motion. Thereby, a desired degree of motion correction accuracy may be achieved, in particular by adapting the threshold in the motion parameters, at which a new scout image is acquired.

According to an embodiment, the k-space data is acquired in a plurality of echo trains, wherein several k-space lines are acquired in one echo train, and wherein each echo train is associated with one motion state of the subject. This assumes that each echo train is associated with the same motion state of the subject. Thus, one set of motion parameters may be estimated for each echo train/motion state/time point i, and all motion states together make up a motion trajectory.

According to an embodiment, each low-resolution scout image is acquired in a time period of less than 3 seconds, e.g., in one echo train. Thereby, it is assured that also each scout image is associated with one motion state of the subject. The scout image may be acquired with a high acceleration factor, e.g., subsampling, as well as with low-resolution. For motion identification, in particular when comparing the scout images with one another in order to detect subject motion between the scout images, or when estimating the motion trajectory of the subject, it may be sufficient to acquire only a fraction of k-space data needed to form a scout image. These few k-space lines may then be compared against corresponding k-space lines of the imaging sequence to determine the occurrence of motion. In particular, each scout image may be acquired within a time period of 0.4 to 3 seconds or 0.8 to 2 seconds.

According to an embodiment, the second act uses at least a part of the k-space data acquired in the acquisition of the scout images, i.e., the scout data. Thus, it is possible (though not necessary) to incorporate scout k-space data into the image reconstruction. Thereby, the scout data may be employed to improve the robustness of the image reconstruction in the final act. This is advantageous, because in the presence of large subject motion, the voxel estimation during the final estimation of the motion-corrected image dataset may become instable. This is because rotations in the image domain correspond to rotations in k-space, and thus these types of patient motion may lead to gaps in k-space, i.e., some portions of k-space have not been sampled during the imaging sequence, because of patient motion. In case of severe patient motion, this kind of inhomogeneous k-space coverage may lead to artifacts despite the availability of accurate information on the motion trajectory. To stabilize this inverse problem, k-space data from the scout scans, together with the corresponding motion information for each scout scan, may be used to supplement the k-space data used in the final act of the image reconstruction, namely the estimation of the motion-corrected image dataset using the motion trajectory and the acquired k-space data. This yields a better-conditioned reconstruction problem and thus improves image quality.

In an embodiment, the imaging sequence provides for sampling of k-space in a sampling order in which the one or several phase-encoding gradients are changed incrementally from one k-space line to the next, e.g., in a linear sampling order, with the exception that a number of k-space lines, (e.g., 2-8 k-space lines), are acquired near the center of k-space in each echo train. Thereby, each echo train has at least a small overlap with the k-space data of the scout scans, which improves the estimation of the motion trajectory. In a linear sampling order, the phase-encoding gradient(s) is/are increased incrementally or step-by-step for each k-space line, resulting in a sampling of k-space line-by-line, from one end of k-space to the other. The k-space lines may be straight k-space lines that are acquired one after the other in a radial, spiral or any other pattern, as viewed in the phase-encode plane.

In an embodiment, the imaging protocol uses a 3D parallel imaging technique, in which one or both of the phase encoding directions are subsampled by a predetermined acceleration factor, and the image dataset is acquired using a multi-channel coil array. Accordingly, the subsampling pattern may be incorporated into the forward model, e.g., a "SENSE+motion" model. In particular, the first act and the second act of the minimization may use a "SENSE+motion" forward model described by $$s_i = E_{\theta_i} x = M_i F C T_{\theta_i} R_{\theta_i} x,$$

In this equation, $s_i$ is the multi-channel k-space data acquired at time point i, in particular in echo train i, x is the MR image. $E_\theta$ is the encoding operator for a given patient motion state $\theta$, wherein at each time point i, the subject's position is described by a new set of six rigid-body motion parameters $\theta_i$ that describe the 3D position of the subject. $R_i$ describes the image rotation at time point i. $T_i$ describes the image translation at time point i, C is a coil sensitivity map. F is the Fourier operator and $M_i$ is the under-sampling mask of the imaging sequence. A similar forward model is described in K. P. Pruessmann et al., "SENSE: sensitivity encoding for fast MRI," Magn. Reson. Med., vol. 42, no. 5, pp. 952-962, 1999.

According to an embodiment, the forward model may be phase-aware, as shown in the below equation:

$$s_i = E_{\theta_i} x = M_i F C T_{\theta_i} R_{\theta_i} e^{i\phi_i} x,$$

In this equation, the operator further includes a term $e^{i\phi_i}$ including the phase variation at each time point i. For example, phase maps $\phi$ dependent on motion state i may be included into the forward model.

In a further aspect, a magnetic resonance imaging apparatus is provided that includes a radio frequency controller configured to drive an RF-coil, e.g., including a multi-channel coil-array, a gradient controller configured to control gradient coils, and a control unit configured to control the radio frequency controller and the gradient controller to execute the imaging sequence. The MRI-apparatus may be a commercially available MRI-apparatus which has been programmed to perform the method disclosed herein. For example, it may be 3T scanner like the MAGNETOM Vida of SIEMENS Healthcare, Erlangen, Germany. A multi-channel coil array may for example be a 32-channel head coil but may also be a coil array for spine-imaging.

According to a further aspect, a computer configured to generate a motion-corrected magnetic resonance image dataset is provided. The computer includes: an interface configured to receive k-space data and scout images acquired according to the method described herein, and a processing unit configured to estimate the motion-corrected image dataset and motion parameters by minimizing the data consistency error between the k-space data acquired in the imaging protocol and a forward model described by an encoding matrix, wherein the encoding matrix includes the effects of motion for each set of additional k-space lines, Fourier encoding, and optionally subsampling and/or coil sensitivities of a multi-channel coil array.

The computer may be any computer including a sufficiently powerful processing unit, which may be a CPU or GPU, or several such processing units. Accordingly, the computer may be a PC, a server, a console of an MRI apparatus, but it also may be a computer that is remote from the MRI apparatus, it may be connected with it through the internet. Accordingly, the computer may also be a cloud computer, a remote server etc. The computer may also be a mobile device, such as a laptop, tablet computer or mobile phone.

According to a further aspect, a computer program is provided which includes program code, which causes a magnetic resonance imaging apparatus—such as the apparatus described herein—to execute the method.

According to a further aspect, a non-transitory computer-readable medium containing a computer program is provided. The computer-readable medium may be any digital storage medium, such as a hard disc, a cloud, an optical medium such as a CD or DVD, a memory card such as a compact flash, memory stick, a USB-stick, multimedia stick, secure digital memory card (SD), etc.

All features of the disclosed method may be embodied in the MRI apparatus, computer, computer program and computer-readable storage medium according to other aspects of the disclosure and vice versa.

BRIEF DESCRIPTION OF THE DRAWINGS

The accompanying drawings illustrate various example methods and other example embodiments of various aspects of the disclosure.

Similar elements are designated with the same reference signs in the drawings.

DETAILED DESCRIPTION

Figure 1:
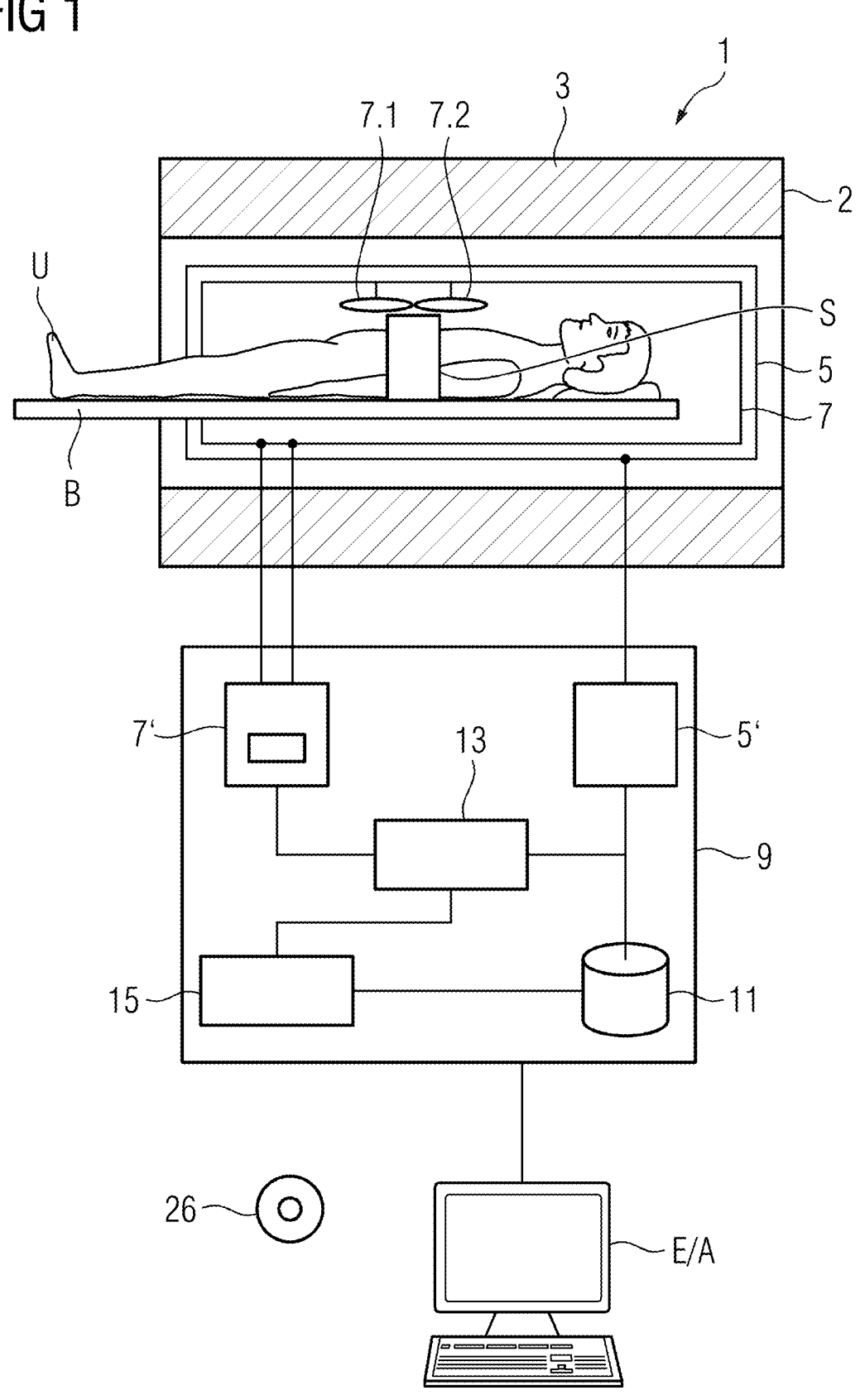
FIG. 1 is a schematic representation of an example of an MRI apparatus.

FIG. 1 schematically shows a magnetic resonance (MR) apparatus 1. The MR apparatus 1 has an MR data acquisition scanner 2 with a magnet 3 that generates the constant magnetic field, a gradient coil arrangement 5 that generates the gradient fields, one or several radio-frequency (RF) antennas 7 for radiating and receiving RF signals, and a control computer 9 configured to perform the method. The radio-frequency antennas 7 may include a multi-channel coil array including at least two coils, (e.g., the schematically shown coils 7.1 and 7.2), which may be configured to transmit and/or receive RF signals (MR signals).

In order to acquire MR data from an examination subject U, (e.g., a patient or a phantom), the examination subject U is introduced on a bed B into the measurement volume of the scanner 2. The slab S is an example of a 3D slab of the examination subject from which MR data may be acquired using a method according to an embodiment. The control computer 9 controls the MR apparatus 1 and may control the gradient coil arrangement 5 with a gradient controller 5' and the RF antenna 7 with a RF transmit/receive controller 7'. The RF antenna 7 has multiple channels corresponding to the multiple coils 7.1, 7.2 of the coil arrays, in which signals may be transmitted or received. The control computer 9 also has an imaging protocol processor 15 that determines the imaging protocol, including the reordering pattern. A control unit 13 of the control computer 9 is configured to execute all the controls and computation operations required for acquisitions. Intermediate results and final results required for this purpose or determined in the process may be stored in a memory 11 of the control computer 9. A user may enter control commands and/or view displayed results, (e.g., image data), via an input/output interface E/A. A non-transitory data storage medium 26 may be loaded into the control computer 9 and may be encoded with programming instructions (program code) that cause the control computer 9, and the various functional units thereof described above, to implement any or all embodiments of the method.

Figure 2:
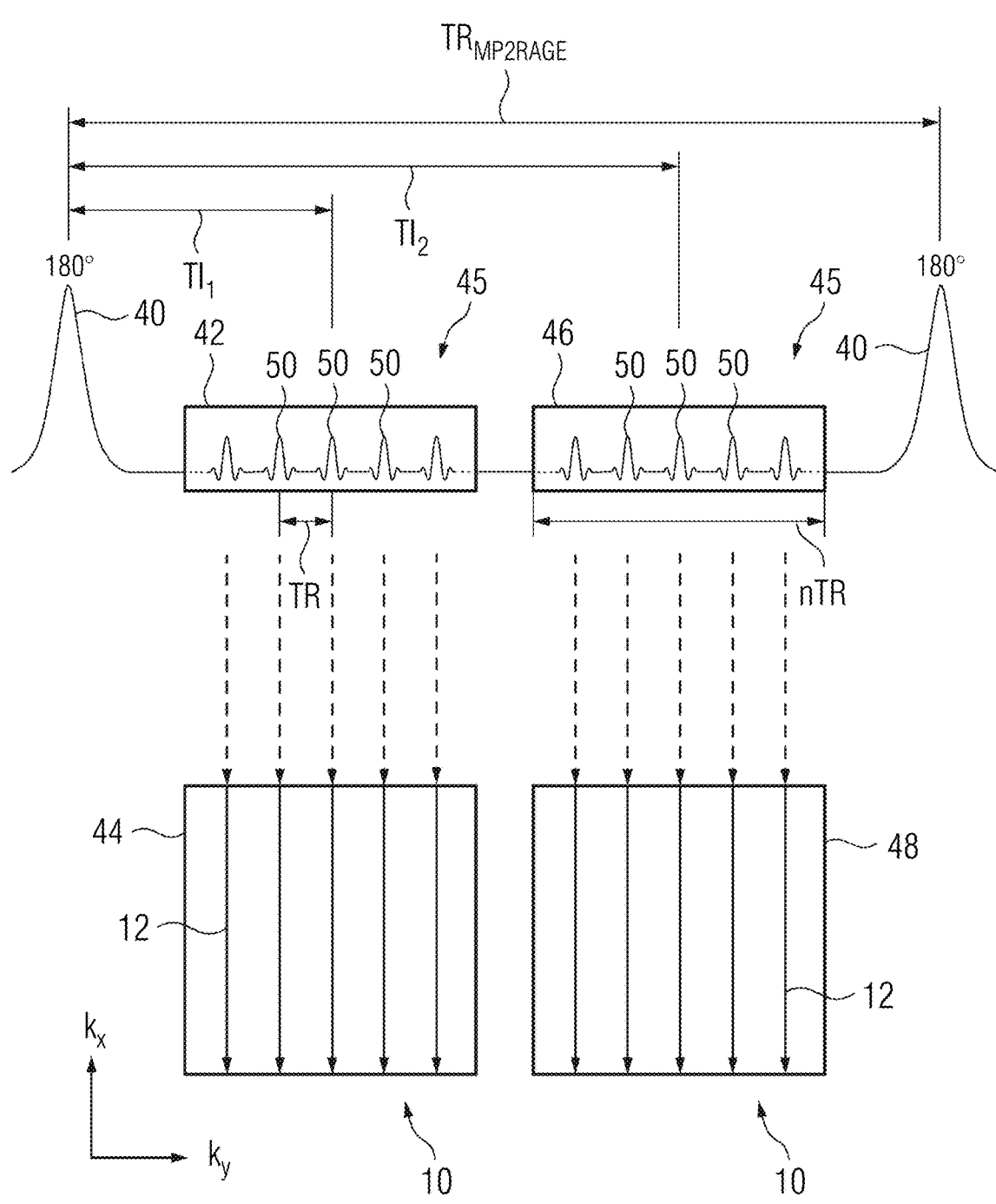
FIG. 2 is a sequence diagram of an example of a MP2RAGE imaging protocol.

FIG. 2 shows a sequence diagram illustrating an MP2RAGE sequence, which is an imaging sequence that may be used in the method. The sequence has a 180° inversion pulse 40 followed by an echo train 45 of gradient echoes 50. The gradients (not shown) include phase-encode gradients and readout gradients, as known in the art. Each of the echoes 50 is used to acquire one k-space line 12 in the k-space 10. However, in MP2RAGE, the echo train 45 is divided into a first part or sub echo train 42, which is used to acquire a first image 44, and a second part or sub-echo train 46, which is used to acquire a second image 48. Thus, each echo 50 in the first part 42 of the echo train 45 is used to acquire one k-space line 12 in the first image, and each echo 50 in the second part 46 is used to acquire one k-space line 12 in the second image 48. After $TR_{MP2RAGE}$, a new inversion pulse 40 is played out and further k-space lines 12 are acquired in each image. The two images 44, 48 have different contrast, as the center of k-space of each image 44, 48 is acquired at a different TI, namely $TI_1$ and $TI_2$.

Figure 3:
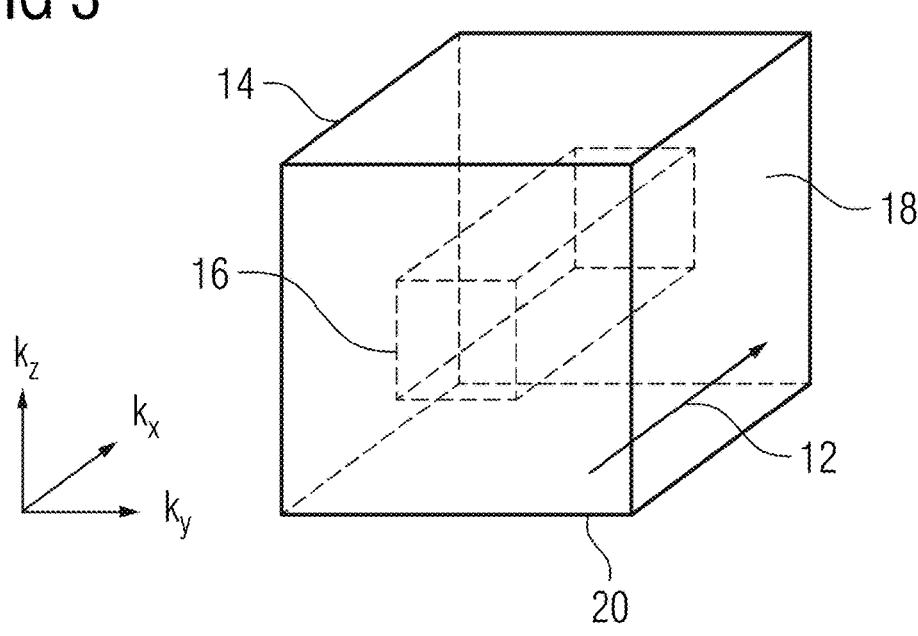
FIG. 3 is a schematic representation of an example of three-dimensional k-space.

In a 3D acquisition, phase encoding is performed in two spatial directions, leading to a distribution of k-space lines 12 across a volume, rather than a plane. FIG. 3 illustrates such three-dimensional k-space 14 having directions $k_x$ in readout direction, and $k_y$ and $k_z$ in the phase encode plane 20. A k-space line acquired during one echo is illustrated at 12. The k-space data for the scout image is acquired in a central region 16, whereas the k-space data for the diagnostic MR image is acquired in the central region 16 and in the periphery 18. Because the full acquisition in readout direction does not cost additional imaging time, the scout region 16 may extend along the full length of the volume in readout direction $k_x$. However, in the phase encode plane 20, which in this illustration is oriented in the plane of the paper, the scout region 16 may cover only about ¼ to ¹⁄₁₆ in each direction, i.e., less than ¹⁄₁₀₀ of the total square phase encode plane 20.

Figure 4:
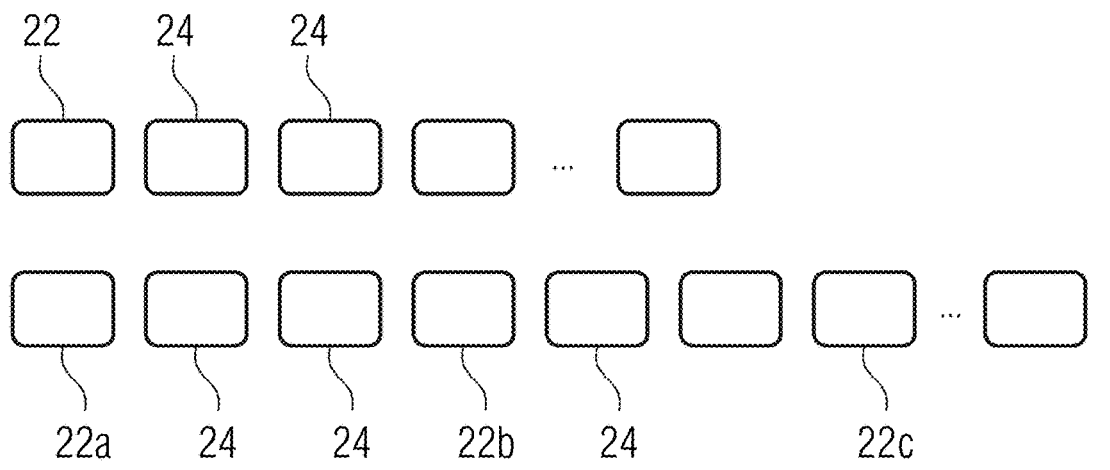
FIG. 4 is a schematic flow diagram of an example of an acquisition method.

FIG. 4 illustrates roughly the sequence of acquisition in a standard SAMER acquisition (above) and according to an embodiment (below). In the standard SAMER sequences, a single scout scan 22 is acquired either before or after the imaging sequence, which is acquired in a number N of shots 24. The single low-resolution scout image is acquired in one shot/echo train 22. In the multi-scout strategy according to an embodiment, multiple scout scans 22*a*, 22*b* and 22*c* are incorporated into the imaging sequence and are acquired in between the shots 24 with which the diagnostic MR data is acquired.

Figure 5:
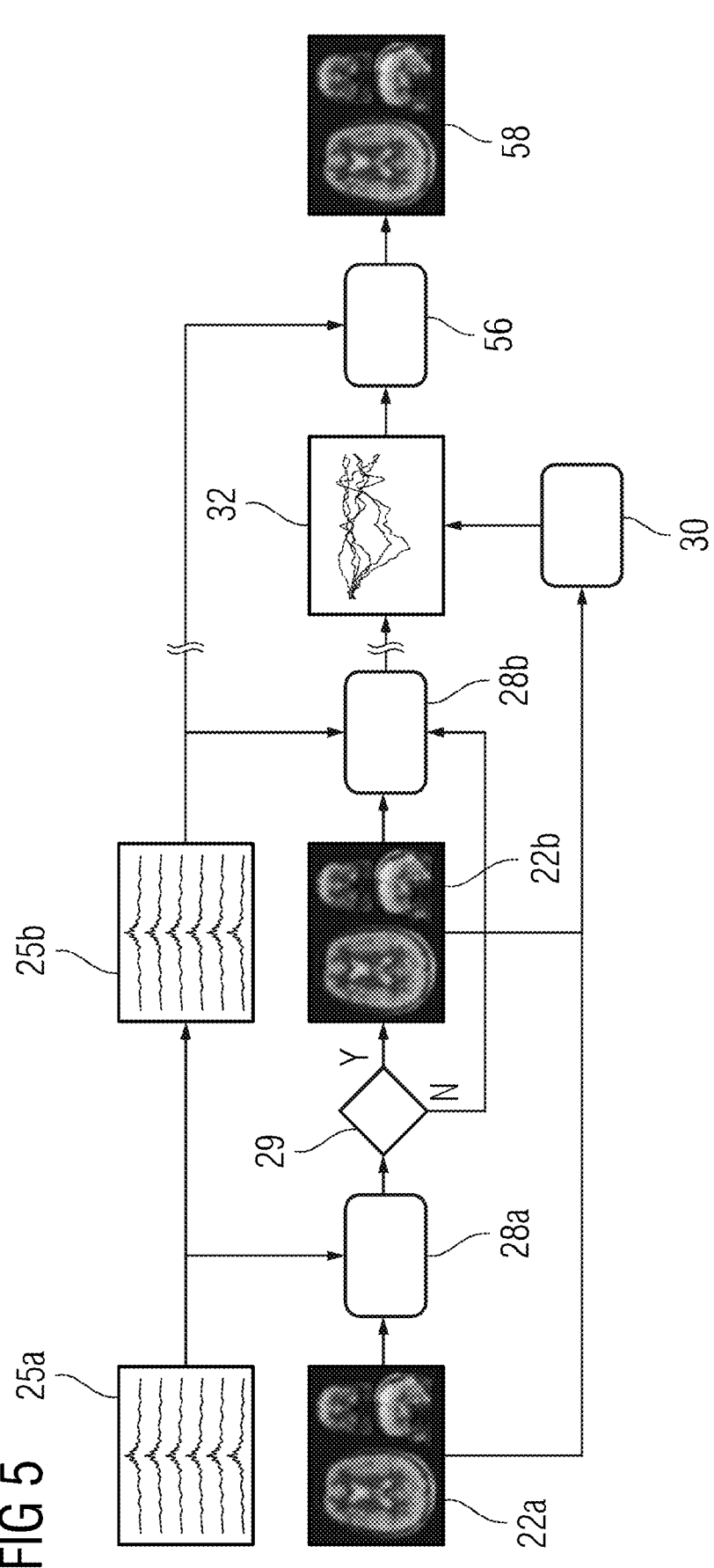
FIG. 5 is a flow diagram of an example of a method.

FIG. 5 gives an overview of an embodiment of the proposed acquisition and reconstruction framework. At first, an ultra-fast (e.g., <3 sec) scout image 22*a* is acquired, e.g., at the beginning/before the imaging sequence. Directly after that, the imaging sequence starts acquiring k-space data 25*a*. While the acquisition goes on, this k-space data 25*a* is compared with the k-space data from the scout scan 22*a* in act 28. This may be done in the first act of the minimization illustrated by equation 54, wherein the scout image 22*a* is taken as an estimate of the motion-corrected image, and the data consistency error between the k-space data 25*a* and a forward model described by the encoding operator $E_\theta$ including the motion trajectory of the subject during the acquisition of the k-space data 25*a* and Fourier encoding is minimized. In this act 28, the magnitude of the patient motion during acquisition of the k-space data 25*a* may be estimated.

If the magnitude of motion is above a certain threshold, a further scout scan 22*b* is acquired. The decision is taken in act 29. If the magnitude of motion is below the threshold, no scout 22*b* is acquired and the method moves on to motion estimation 28*b*, in which the first scout scan 22*a* is compared against the further acquired k-space data 25*b*. The k-space data 25*a*, 25*b*, etc. together form the k-space data of the MR image of the subject that is to be motion-corrected. This may be a high-resolution, diagnostic MR image.

The method thus continues with acquiring k-space data 25, interleaved with further scout scans 22, if required. Either during or after this acquisition, the scout scan 22*a*, 22*b* and optionally further scout scans are registered with one another in act 30. This may be performed in the image domain, wherein rigid or non-rigid motion parameters may be determined between the respective scout scans, or between each scout scan and a first scout scan, e.g. scout 22*a*. These motion parameters between the scout scans are used in the motion estimation 32, wherein the motion trajectory of the subject during acquisition of the k-space data 25, as evaluated in the motion estimation acts 28, is corrected by the motion parameters between the scout images 22.

The resulting motion trajectory of the subject 32 is used in the final motion correction reconstruction 56, corresponding to the second act of the reconstruction and minimization act. Thereby, a corrected image 58 is determined by minimizing the data-consistency error between the k-space data 25 and a forward model, taking into account the estimated motion trajectory 32.

Figures 6, 7:
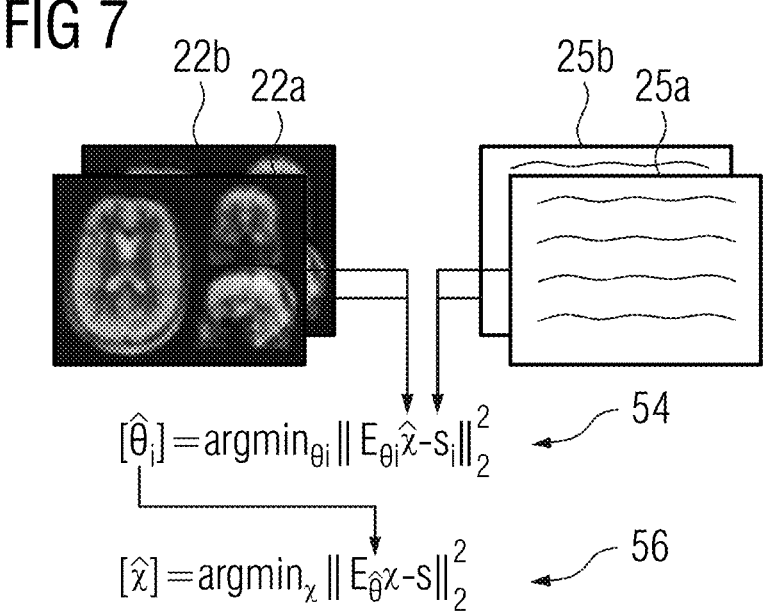
FIG. 6 is an illustration of an example of an alternating optimization algorithm.
FIG. 7 is an illustration of an example of a SAMER optimization.

A retrospective motion correction and image reconstruction technique according to an embodiment is now described mathematically with reference to FIGS. 6 and 7. The mathematical model used is an extension of SENSE parallel imaging, as described in the above-cited paper by K. P.

Pruessmann et al., with rigid-body motion parameters included into the forward model. The forward model or encoding operator $E_\theta$ for a given patient motion vector $\theta$ (including motion parameters over time) relates the motion-free image x to the acquired multi-channel k-space data s. At each time point i that is considered, e.g., the acquisition time of the sets of guidance lines, the subject's position is described by a new set of six rigid-body motion parameters $\theta_i$ that describe the 3D position of the subject. Accordingly, the multi-channel k-space data $s_i$ acquired at time point i may be related to the 3D image volume x through image rotations $R_i$, image translations $T_i$, coil sensitivity maps C, Fourier operator F and under-sampling mask $M_i$ by the following formula 1:

$$s_i = E_{\theta_i} x = M_i F C T_{\theta_i} R_{\theta_i} x. \qquad [1]$$

A phase operator $e^{i\phi_i}$ may also be included. In prior art methods, as illustrated in FIG. 6, both the motion corrected image vector x and the motion vector (trajectory) $\theta$ are estimated by performing an alternating, repeated optimization between the image vector (formula 2) and the motion vector (formula 3):

$$[\hat{x}] = \text{argmin}_x \left\| E_\theta x - s \right\|_2 \qquad [2]$$

$$[\hat{\theta}] = \text{argmin}_\theta \| E_\theta \hat{x} - s \|_2 \qquad [3]$$

This may lead to convergence issues as updates of x and $\theta$ will be computed on inaccurate information. Moreover, the reconstruction is computationally demanding as repeated updates of x (millions of imaging voxels) are needed.

Using several ultra-fast low-resolution scout scans 22*a*, 22*b*, the motion trajectory may be directly estimated, as illustrated in FIG. 7, thus avoiding the time-consuming alternate optimization. A scout image 22*a*, designated by $\tilde{x}$, approximates the motion-free image volume x and each motion state may be determined independently by minimizing the data consistency error of the forward model:

$$[\hat{\theta}_i] = \text{argmin}_{\theta_i} \left\| E_{\theta_i} \tilde{x} - s_i \right\|_2 \qquad [4]$$

In the method, the k-space lines 25*a*, 25*b* acquired close in time to each scout image 22*a*, 22*b* may be used as $s_i$ in this first act of the optimization. Several scout images 22*a*, 22*b* may be used for different parts of k-space 25*a*, 25*b*. Once this optimization is completed, the resulting motion parameters $\theta_i$ may be corrected by the subject motion between the several scout images, which has been obtained by registration of the scout images with one another. Thereby, a motion state of the patient may be estimated for each echo train, resulting in a motion trajectory $\theta_i$ for all motion states i.

For the final image reconstruction, the motion states from each shot are combined and the motion-mitigated image is obtained from solving a standard least-squares problem:

$$[\hat{x}] = \text{argmin}_x \left\| E_{\hat{\theta}} x - s \right\|_2 \qquad [5]$$

This strategy completely avoids the difficult non-linear and non-convex joint optimization that contains millions of unknowns, as it only considers six rigid body parameters per motion optimization, and it does not require computationally costly full or partial updates to the image. The encoding operator $E_{\theta_i}$ may also include phase information so that the model is phase-aware.

This framework may also be extended to Wave-CAIPI encoding. This method exploits available information in modern multi-channel receivers and may provide up to R=9-fold speedup for many important clinical contrasts. The sinusoidal gradients in Wave-encoding lead to a spatially varying phase that is applied along the read-out in hybrid space. Using the notation from the encoding model of formula [1]

$$E_{\theta_i} = M_i F_{y,z} P_{yz} F_c CT_{\theta_i} R_{\theta_i} \qquad [6]$$

In this equation, the Fourier transform has been modified to contain the Wave point-spread-function $P_{yz}$. A phase operator $e^{i\Phi_i}$ may also be included.

Figure 8:
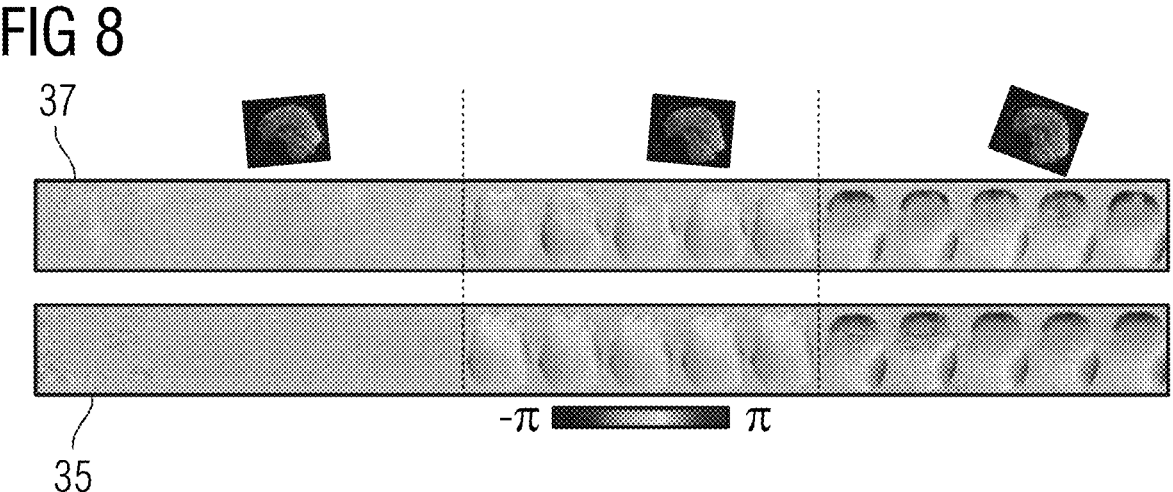
FIG. 8 illustrates the evolution of an example of phase differences caused by patient motion during image acquisition.

Finally, FIG. 8 illustrates the estimation of the phase-evolution, which may be performed using the multiple scout scans. The images 35, 37 show the phase variations in an axial image of a human head caused by motion in a gradient echo imaging sequence using an echo time of 25 ms. The subject was asked to change its pose twice during the acquisition, resulting in three poses, pose 1, pose 2, and pose 3. The lower images 35 show the ground truth of the phase evolution, i.e. the phase does not change while the subject is in the first pose, and changes significantly after the motion towards the second pose and again after the subject moves into the third pose. The upper images 37 show the phase evolution as obtained by a low-rank phase estimation approach.

In act 1, k-space data is synthesized for each motion state using the current image estimate and the SENSE+motion model.

In act 2, acquired k-space data is used to partially replace/substitute synthesized k-space data in each motion state. Note, only a small amount of acquired imaging and scout k-space data will be available from each motion state.

In act 3, the SENSE+model is used to transform the new k-space data back to image space and obtain projection images for each motion state.

In act 4, a low-rank phase approximation approach (e.g., ESPIRiT (https://pubmed.ncbi.nlm.nih.gov/23649942/)) is used to estimate the desired phase changes across the projection images.

In act 5, a refined image estimate may be computed using a phase-aware SENSE+motion model and the estimated phase variation across the motion states. Further image improvement may be achieved by repeatedly iterating acts 1-5.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a motion-corrected magnetic resonance (MR) image dataset of a subject, the method comprising:
   acquiring k-space data of an MR image of the subject in an imaging sequence;
   acquiring at least two scout images of the subject that are interleaved with the k-space data of the imaging sequence;
   comparing the at least two scout images with one another in order to detect and/or to estimate subject motion between the at least two scout images; and
   reconstructing a motion-corrected MR image dataset from the k-space data acquired in the imaging sequence by minimizing a data consistency error between the k-space data and a forward model described by an encoding operator,
   wherein the encoding operator comprises a motion trajectory of the subject during the imaging sequence, Fourier encoding, and optionally a phase operator, subsampling, and/or coil sensitivities of a multi-channel coil array, and
   wherein the minimizing of the data consistency error is executed by:
      estimating the motion trajectory of the subject by comparing at least part of the k-space data with at least one scout image of the at least two scout images taking into account the detected subject motion or the estimated subject motion between the at least two scout images; and
      estimating the motion-corrected MR image dataset using the estimated motion trajectory,
      wherein both the estimating of the motion trajectory and the estimating of the motion-corrected MR image dataset comprise a minimization of the data consistency error between at least part of the acquired k-space data and the forward model.

2. The method of claim 1, wherein the estimating of the subject motion between the at least two scout images comprises registering the at least two scout images with one another to detect subject motion between the at least two scout images, and
   wherein the motion trajectory of the subject is estimated by comparing the part of the k-space data acquired before and/or after each scout image of the at least two scout images with the respective scout image in order to estimate the motion trajectory of the subject during an acquisition of the respective part of the k-space data and correcting the motion trajectory with the subject motion between the at least two scout images.

3. The method of claim 1, wherein the estimating of the subject motion between the at least two scout images comprises registering a second scout image and optionally each further scout image with a first scout image to estimate motion parameters between the at least two scout images,
   wherein the motion trajectory of the subject is estimated by comparing the acquired k-space data with the first scout image, and wherein the minimizing of the data consistency error uses the motion parameters estimated from the registering as a starting estimate for the motion trajectory for the part of the k-space data acquired before and/or after the second scout image and optionally each further scout image.

4. The method of claim 1, wherein the forward model is phase-aware and comprises effects of changes in a B0 field caused by subject motion during the imaging sequence.

5. The method of claim 4, wherein at least one map of phase differences is calculated between a first scout image and a second scout image and optionally one or more further scout images of the at least two scout images, and wherein the at least one map of the phase differences is used in a phase-aware estimation of the motion-corrected MR image dataset.

6. The method of claim 1, wherein a time interval between the acquisition of the at least two scout images during the imaging sequence is dynamically adapted depending on whether subject motion is detected.

7. The method of claim 1, wherein the estimating of the motion trajectory is carried out during an image acquisition, and wherein a time interval to an acquisition of a next scout image is adapted depending on whether the estimated motion trajectory indicates a strong subject motion or a weak subject motion.

8. The method of claim 1, wherein the k-space data is acquired in a plurality of echo trains, wherein several k-space lines are acquired in one echo train, and wherein each echo train of the plurality of echo trains is associated with one motion state of the subject.

9. The method of claim 1, wherein the estimating of the motion-corrected MR image dataset uses at least a part of the k-space data acquired during the acquiring of the at least two scout images.

10. The method of claim 1, wherein the imaging sequence uses a parallel imaging technique in which k-space is subsampled by a predetermined acceleration factor, wherein the image dataset is acquired using the multi-channel coil array, wherein the estimating of the motion trajectory and the estimating of the motion-corrected MR image dataset in the minimizing of the data consistency error use the forward model described by:

$$s_i = E_{\theta_i} x = M_i F C T_{\theta_i} R_{\theta_i} x,$$

wherein:

$s_i$ is multi-channel k-space data acquired at time point i;

x is the MR image;

$E_\theta$ is the encoding operator for a given patient motion state $\theta$, wherein at each time point i, a 3D position of the subject is described by a new set of six rigid-body motion parameters $\theta_i$;

$R_{\theta_i}$ describes an image rotation at the time point i;

$T_i$ describes an image translation at the time point i;

C is a coil sensitivity map;

F is a Fourier operator; and $M_i$ is an under-sampling mask of the imaging sequence.

11. The method of claim 10, wherein the encoding operator comprises the phase operator.

12. A magnetic resonance (MR) imaging apparatus comprising:

a radio frequency controller configured to drive an RF-coil comprising a multi-channel coil array;

a gradient controller configured to control gradient coils;

a control unit configured to control the radio frequency controller and the gradient controller to execute an imaging sequence, wherein the control unit is configured to:

acquire k-space data of an MR image of a subject in the imaging sequence;

acquire at least two scout images of the subject that are interleaved with the k-space data of the imaging sequence;

compare the at least two scout images with one another in order to detect and/or to estimate subject motion between the at least two scout images; and reconstruct a motion-corrected MR image dataset from the k-space data acquired in the imaging sequence via a minimization of a data consistency error between the k-space data and a forward model described by an encoding operator, wherein the encoding operator comprises a motion trajectory of the subject during the imaging sequence, Fourier encoding, and optionally a phase operator, subsampling, and/or coil sensitivities of the multi-channel coil array, and wherein the minimization of the data consistency error is executed by:

an estimation of the motion trajectory of the subject by comparing at least part of the k-space data with at least one scout image of the at least two scout images taking into account the detected subject motion or the estimated subject motion between the at least two scout images; and an estimation of the motion-corrected MR image dataset using the estimated motion trajectory, wherein both the estimation of the motion trajectory and the estimation of the motion-corrected MR image dataset comprise a minimization of the data consistency error between at least part of the acquired k-space data and the forward model.

13. A non-transitory computer readable medium comprising a computer program including program code, wherein the program code, when executed by a control unit of a magnetic resonance (MR) imaging apparatus, causes the magnetic resonance imaging apparatus to:

acquire k-space data of an MR image of a subject in an imaging sequence;

acquire at least two scout images of the subject that are interleaved with the k-space data of the imaging sequence;

compare the at least two scout images with one another in order to detect and/or to estimate subject motion between the at least two scout images; and reconstruct a motion-corrected MR image dataset from the k-space data acquired in the imaging sequence via a minimization of a data consistency error between the k-space data and a forward model described by an encoding operator, wherein the encoding operator comprises a motion trajectory of the subject during the imaging sequence, Fourier encoding, and optionally a phase operator, subsampling, and/or coil sensitivities of a multi-channel coil array, and wherein the minimization of the data consistency error is executed by:

an estimation of the motion trajectory of the subject by comparing at least part of the k-space data with at least one scout image of the at least two scout images taking into account the detected subject motion or the estimated subject motion between the at least two scout images; and an estimation of the motion-corrected MR image dataset using the estimated motion trajectory, wherein both the estimation of the motion trajectory and the estimation of the motion-corrected MR image dataset comprise a minimization of the data consistency error between at least part of the acquired k-space data and the forward model.

\* \* \* \* \*